United States Patent
Long (10) Patent No.: US 12,232,932 B2
(45) Date of Patent: Feb. 25, 2025

(54) MEDICATED THREAD DRAINAGE THERAPY APPARATUS

(71) Applicant: Dan Long, Changsha (CN)

(72) Inventor: Dan Long, Changsha (CN)

( * ) Notice: Subject to any disclaimer, the term of this patent is extended or adjusted under 35 U.S.C. 154(b) by 737 days.

(21) Appl. No.: 17/595,506

(22) PCT Filed: Jun. 17, 2020

(86) PCT No.: PCT/CN2020/096588
§ 371 (c)(1),
(2) Date: Nov. 18, 2021

(87) PCT Pub. No.: WO2020/259367
PCT Pub. Date: Dec. 30, 2020

(65) Prior Publication Data
US 2022/0265476 A1 Aug. 25, 2022

(30) Foreign Application Priority Data
Jun. 26, 2019 (CN) .......................... 201910562453.6

(51) Int. Cl.
*A61F 13/00* (2024.01)
*A61F 13/05* (2024.01)
*A61M 1/00* (2006.01)

(52) U.S. Cl.
CPC ........ *A61F 13/00063* (2013.01); *A61F 13/05* (2024.01); *A61M 1/91* (2021.05);
(Continued)

(58) Field of Classification Search
CPC ................ A61F 13/00063; A61F 13/05; A61F 2013/00536; A61F 2013/00936; A61M 1/91
(Continued)

(56) References Cited

U.S. PATENT DOCUMENTS

| 2005/0015042 A1* | 1/2005 | Sun ...................... A61N 1/0428 |
| | | 977/932 |
| 2007/0208280 A1* | 9/2007 | Talish ...................... A61N 7/00 |
| | | 29/25.35 |

(Continued)

FOREIGN PATENT DOCUMENTS

| CN | 101991484 A | 3/2011 |
| CN | 102836503 A | 12/2012 |

(Continued)

OTHER PUBLICATIONS

ISR of PCT/CN2020/096588.

*Primary Examiner* — Andrew J Mensh
(74) *Attorney, Agent, or Firm* — Hemisphere Law, PLLC; Zhigang Ma (57) ABSTRACT

The present disclosure belongs to the field of treatment devices, and specifically relates to a medicated thread drainage treatment device. The treatment device includes a first treatment unit used for postoperative pain relief and drainage; a second treatment unit used for promoting quick healing of a wound; a third treatment unit used for preventing deep venous thrombosis; and an electropneumatic, negative-pressure, electric stimulation multipurpose therapy apparatus connected with the first treatment unit, the second treatment unit, and the third treatment unit and providing electropneumatic pressure, negative pressure, and electric energy. The present disclosure is used for postoperative quick healing and recovery; promotion of clinical use guidelines will greatly reduce and even eliminate the postoperative complications, particularly postoperative complications of pulmonary embolism, thus saving patients' lives.

9 Claims, 4 Drawing Sheets

(52) U.S. Cl.
CPC ............... *A61F 2013/00536* (2013.01); *A61F 2013/00936* (2013.01)

(58) Field of Classification Search
USPC ......................................................... 604/543
See application file for complete search history.

(56) References Cited

U.S. PATENT DOCUMENTS

| | | | | |
|---|---|---|---|---|
| 2009/0112283 | A1* | 4/2009 | Kriksunov | A61N 1/205 607/66 |
| 2010/0057025 | A1* | 3/2010 | Aicher | A61M 1/734 604/319 |
| 2010/0204752 | A1* | 8/2010 | Tremblay | A61M 1/92 604/543 |
| 2011/0034906 | A1* | 2/2011 | Malhi | A61F 13/0209 604/543 |

FOREIGN PATENT DOCUMENTS

| | | |
|---|---|---|
| CN | 202859914 U | 4/2013 |
| CN | 204745115 U | 11/2015 |
| CN | 105497993 A | 4/2016 |
| CN | 106039557 A | 10/2016 |
| CN | 107281640 A | 10/2017 |
| CN | 110368583 A | 10/2019 |
| WO | 2010093753 A1 | 8/2010 |

* cited by examiner

MEDICATED THREAD DRAINAGE THERAPY APPARATUS

TECHNICAL FIELD

The present disclosure belongs to the field of treatment devices, and specifically relates to a medicated thread drainage treatment device.

BACKGROUND

At present, all methods for postoperative pain relief are drug administration via oral administration, vein, intramuscular injection, spinal canal, and an analgesic pump. Postoperative pain relief by drugs causes a series of side effects such as drowsiness and muscular relaxation of both lower extremities of a patient, which may cause deep venous thrombosis. In addition, to dispose operative wounds, there is no substantive therapy except for disinfecting the wounds and changing gauze and dressing. Hydrops and damaged tissue factors such as wound debris and fat granules in a subcutaneous operative area of a wound cannot be extracted and will be circulated to the lower extremities with the blood, which may cause deep vein thrombosis and fat embolism in the lower extremities. These are very detrimental to quick recovery of an operative wound. Ceaselessly negative pressure drainage may block a pipe under the influence of tissue coagulation, or is hindered because a wound direction (such as a dendritic wound) is opposite to a negative pressure drainage direction, which leads to pain in the wound, becoming a defect in negative pressure drainage. The incidence of systemic complications (such as cardio-pulmonary dysfunction and venous thrombosis) of a patient after a surgical operation such as abdominal operation is still up to 20%-60%. In some cases, although the operation is performed safely, the treatment results are not satisfactory. The patient has postoperative complications and even loses his life. Therefore, the surgeon has sometimes faced an "embarrassing" situation of "successful operation, failure in treatment, and even patients losing their lives". In any hospital, this kind of situation is by no means rare. Although there are clinical prevention guidelines for traumatic complications, such as deep vein thrombosis, caused by operations, the deep vein thrombosis still occurs frequently after the operation, and quick healing and recovery of the wound cannot be well achieved.

Therefore, in view of the above deficiencies, it is necessary to provide a technical solution to overcome or at least alleviate the deficiencies in the existing art.

SUMMARY

In order to solve the above problems, the present disclosure provide a medicated thread drainage treatment device. The treatment device is a new multi-mode treatment technology that is convenient to use and has a definite therapeutic effect. Its technological treatment core is as follows. I, six major pain relief modes such as postoperative multi-mode mechanical electronarcosis, placement of a medical thread in a negative pressure pipe for drainage, medicated thread infiltration anesthesia, paste penetration for pain relief, "electric energy promotes relief of inter-nerve edema", and retrogradation extraction of hydrops in the operative area are provided. II, many therapies are provided to promote quick healing of a wound: healing the wound by electrical stimulation, promoting the blood circulation, supplying oxygen to the wound, covering the wound by positive charges such as potassium ions, calcium ions, and magnesium ions, and extracting the hydrops in the operative area of the wound by medicated thread negative pressure. III, many methods are provided to eliminate the pathogenesis of the deep venous thrombosis. Many methods include six major methods: (1) by drainage with the electric energy, the medicated threads, and negative pressure, the hydrops and damaged tissue factors (such as wound debris, fat granules, and metabolites) in the operative area of the wound retrograde smoothly and are quickly and fully extracted, without entering the blood, so as to avoid them from entering the blood circulation and going into both lower extremities, which will cause venous thrombi in the lower extremities and fat embolism; (2) blood coagulation factors are electrically interfered to be quickly decomposed; (3) crus muscles are electrically stimulated, thus promoting muscle shrinkage and accelerate venous blood flow; (4) the electric energy accelerates healing, so the number of blood coagulation factors is reduced; (5) by electroanalgesia, activities cannot be affected; and (6) the crus is electrically pressed so that the returned blood volume is increased. The present disclosure is used for postoperative quick healing and recovery; promotion of clinical use guidelines will greatly reduce and even eliminate the postoperative complications, particularly postoperative complications of pulmonary embolism, thus saving patients' lives.

The present disclosure is realized by the following technical solution:

A medicated thread drainage treatment device, including:
- a first treatment unit used for postoperative pain relief, preferably multi-mode pain relief, wherein the multi-mode pain relief of the first treatment unit refers to clinically selecting a suitable pain relief mode from various pain relief modes, and the multi-mode pain relief includes two or more of electronarcosis for pain relief, infiltration anaesthesia, medicated thread drainage for pain relief, and paste penetration for pain relief;
- a second treatment unit used for promoting a wound to be quickly healed, wherein multiple therapies are preferably used to promote the wound to be quickly healed; promotion of quick healing of the wound by multiple therapies refers to clinically selecting suitable therapies from various methods that promote the wound to be quickly healed; the multiple therapies include promoting the blood circulation, electrical stimulation, oxygen supply, coverage with positive charges, and negative pressure extraction of hydrops in an operative area of the wound by means of a medicated thread;
- a third treatment unit used for preventing deep venous thrombosis, wherein multiple methods are preferably used to prevent the deep venous thrombosis, and include two or more of the following methods: (1) the wound is comprehensively drained with the electric energy, the medicated thread, and the negative pressure so that the hydrops and damaged tissue factors in an operative area seep; (2) blood coagulation factors are electrically interfered to be quickly decomposed; (3) crus muscles are electrically stimulated, thus promoting muscle shrinkage and accelerating venous blood flow; (4) the electric energy accelerates healing, so the number of blood coagulation factors is reduced; (5) by electroanalgesia, activities cannot be affected; and (6) the crus is electrically pressed so that the returned blood volume is increased;
- an electropneumatic, negative pressure, electric stimulation multipurpose therapy apparatus connected with the first treatment unit, the second treatment unit, and the third treatment unit and providing electropneumatic pressure, negative-pressure, and electric energy.

Further, the first treatment unit includes a first medicated thread, a first non-woven fabric, a first water absorption pad, two first suction pipe disks, a first negative pressure pipe used to be connected with a negative pressure suction device to suck liquid on the wound, a first pressure reducing pipe, and two first metal wire sockets;

the first water absorption pad is arranged at the middle position on the first non-woven fabric; the first medicated thread is arranged on the first water absorption pad; disk parts of the two first suction pipe disks are respectively arranged at two ends of the first water absorption pad; a pipe part of one first suction pipe disk is connected with the first negative pressure pipe, and a pipe part of the other first suction pipe disk is connected with the first pressure reducing pipe or a rinser; and the two first metal wire sockets (by means of hydrogel) are respectively arranged at two corners of the first non-woven fabric and are respectively connected with the electropneumatic, negative-pressure, electric stimulation multipurpose therapy apparatus.

Further, first glue is uniformly coated on the first non-woven fabric on the surface with the first water absorption pad to fix the first medicated thread and the first water absorption pad which cover the wound.

Further, the first water absorption pad is fixed on the first non-woven fabric through the first glue, and the first medicated thread is fixed on the first water absorption pad through the first glue.

Further, the first medicated thread is not infiltrated with drugs when used in a nonoperative wound, is infiltrated with lidocaine cream when used in wound infiltration anesthesia, and is infiltrated with a first blend when used in wound pain relief.

Further, the first blend includes *rhizoma corydalis*, eggplants, *fructus meliae toosendan, rhizoma kaempferiae, rhizoma chuanxiong, Angelica sinensis, Rheum officinale, asarum, Ferula asafoetida*, olibanum, *Radix curcuma*, diclofenac sodium, semen strychni, borneol, cape jasmine, *Radix angelicae* dahuricae, and *Radix scutellariae*, each of which is 10 grams, fennel, myrrh, *Flos caryophylli*, red peony roots, *Radix aucklandiae, cortex phellodendri*, peppermint oil, and wintergreen oil, each of which is 5 grams, musk and capsicol, each of which is 3 grams, and 1 gram of diphenhydramine.

Further, the first blend is mixed in the first glue.

Further, the second treatment unit includes a second medicated thread, a second non-woven fabric, a second water absorption pad, two second suction pipe disks, a second negative pressure pipe used to be connected with a negative pressure suction device to suck liquid on the wound, an oxygen supply pipe used for supplying oxygen to the wound, a riser used for rinsing the wound, and two second metal wire sockets;

the second water absorption pad is arranged at the middle position on the second non-woven fabric; the second medicated thread is arranged on the second water absorption pad; disk parts of the two second suction pipe disks are respectively arranged at two ends of an edge of the same side of the second water absorption pad; a pipe part of one second suction pipe disk is connected with the second negative pressure pipe, and a pipe part of the other second suction pipe disk is connected with the oxygen supply pipe and the rinser, respectively; and the two second metal wire sockets (by means of hydrogel) are respectively disposed on the second non-woven fabric and arranged on two sides of the second water absorption pad and are respectively connected with the electropneumatic, negative-pressure, electric stimulation multipurpose therapy apparatus.

Further, a second blend or metal ions is or are adhered on the second medicated thread.

Further, the second water absorption pad is fixed on the second non-woven fabric through the second glue, and the second medicated thread is fixed on the second water absorption pad through the second glue.

Further, the second glue is uniformly coated on the second non-woven fabric on the surface with the second water absorption pad to fix the second medicated thread and the second water absorption pad which cover the wound.

Further, a second blend or metal ions is or are mixed in the second glue.

Further, the second blend includes natural calculus bovis, camphor, pearls, red halloysite, amber, lead monoxide, olibanum, and myrrh, each of which is 8 grams, calcined calamine, calcined plaster, keels, and calomel, each of which is 15 grams, and 15 grams of borneol.

Further, the third treatment unit includes a wound treatment module used on the wound and two auxiliary treatment modules pasted on the crus muscles of the lower extremities;

the wound treatment module and the auxiliary treatment modules are respectively connected with the electropneumatic, negative-pressure, electric stimulation multipurpose therapy apparatus.

Further, the wound treatment module and the auxiliary treatment modules are respectively connected with the electropneumatic, negative-pressure, electric stimulation multipurpose therapy apparatus, so that wound seepage will not be coagulated by means of electrostimulation and the medicated thread and drained smoothly; the damaged tissue factors and the fat granules are extracted from the wound and prevented from entering the blood to cause the deep venous thrombosis and the fat embolism.

Further, a method for preventing the deep venous thrombosis by the third treatment unit includes the following steps: (1) the wound is comprehensively drained with the electric energy, the medicated thread, and the negative pressure so that the hydrops and damaged tissues in the operative area are extracted; (2) blood coagulation factors are electrically interfered to be quickly decomposed; (3) the crus muscles are electrically stimulated, thus promoting muscle shrinkage and accelerating venous blood flow; (4) the electric energy accelerates healing, so the number of blood coagulation factors is reduced; (5) by electroanalgesia, activities cannot be affected; and (6) the crus is electrically pressed so that the returned blood volume is increased.

Further, the wound treatment module includes a third medicated thread, a third non-woven fabric, a third water absorption pad, a third suction pipe disk, a third negative pressure pipe used to be connected with a negative pressure suction device to suck liquid on the wound, and two third metal wire sockets;

the third water absorption pad is arranged at the middle position on the third non-woven fabric; the third medicated thread is arranged on the third water absorption pad; the third suction pipe disk is arranged at the middle part on the third water absorption pad and is connected with the third negative pressure pipe; and the two third metal wire sockets (by means of hydrogel) are respectively disposed on the third non-woven fabric and arranged on two sides of the third water absorption pad and are respectively connected with the electropneumatic, negative-pressure, electric stimulation multipurpose therapy apparatus.

Further, each auxiliary treatment module includes a fourth medicated thread, a fourth non-woven fabric, a fourth water absorption pad, an air bag, and two fourth metal wire sockets;

the fourth water absorption pad is arranged at the middle position on the fourth non-woven fabric; the fourth medicated thread is arranged on the fourth water absorption pad; the two fourth metal wire sockets (by means of hydrogel) are respectively disposed on the fourth non-woven fabric and arranged on two sides of the fourth water absorption pad and are respectively connected with the electropneumatic, negative-pressure, electric stimulation multipurpose therapy apparatus; and the air bag is arranged on the other surface of the fourth non-woven cloth that is opposite to the fourth water absorption pad.

Further, the third medicated thread is blended with a third blend used for treating hypercoagulable high-risk patients and having an effect of activating blood circulation to dissipate stasis;

the third blend includes pseudo-ginseng, *Flos carthami, fructus citri, Radix astragali, Radix codonopsis, rhizoma chuanxiong, pericarpium citri reticulatae viride*, semen *pruni persicae, Radix paeoniae rubra, fructus aurantii*, and *rhizoma cyperi*, each of which is 10 grams, *salvia miltiorrhiza*, pollen typhae, white atractylodes rhizome, yam, olibanum, *Radix bupleuri*, toosendan fruit, *Radix pseudostellariae*, and prepared *Radix* licorice, each of which is 8 grams, and 1 gram of acetylsalicylic acid.

Further, the third medicated thread is used for treating non-hypercoagulable low-risk patients when it is not blended with the third blend.

Further, the hydrogel is blended with the metal ions. When covering the wound, the hydrogel blended with the metal ions adsorbs and activates negatively charged growth factors and protease to be accumulated towards the wound to accelerate healing of the wound. Effusions in the operative area are drained in a retrograde manner by means of energy conduction resonance of the medicated thread and the potassium ions of the hydrogel.

Further, the metal ions are the potassium ions or mixed ions of the potassium ions, sodium ions, calcium ions, and magnesium ions.

Further, a main physiological function of the potassium ions is to maintain the metabolism of cells and activate the activity of the protease;

the sodium ions contribute to the normal operation of nerves and muscles in the body;

the calcium ions are blood coagulation factors and activate the blood coagulation factors to participate in a coagulation process;

the magnesium ions are used for activating the activities of various human enzymes.

Further, the fourth medicated thread is blended with the third blend or is not blended with any drug.

Further, the first non-woven fabric, the second non-woven fabric, the third non-woven fabric, and the fourth non-woven fabric can all be replaced by PU films.

Further, the first glue is hot melt glue.

Further, the second glue is a hot melt glue or autologous blood freeze-dried construct (stem cell).

The present disclosure has the following beneficial effects.

The medicated thread drainage treatment device of the present disclosure includes the first treatment unit, the second treatment unit, and the third treatment unit. A clinician can select the corresponding treatment unit according to a clinical need. The drugs in the first medicated thread in the first treatment unit are mostly analgesia and local anesthesia type drug formulas and are used for infiltration pain relief; the drugs in the second medicated thread in the second treatment unit are mostly wound healing type formulas and used for quickly healing the wound; and the drugs in the third treatment unit are mostly drug formulas for activating blood to dissipate stasis, and the medicated thread is plugged into the wound for anticoagulant drainage. The medicated thread drainage treatment device is used for realizing quick multi-mode pain relief of chronic complex wounds and postoperative wounds and realizing multi-therapy-based quick recovery and healing of the wounds. Multiple methods prevent the postoperative deep vein thrombosis and the fat embolism, and the postoperative complications are greatly reduced; and particularly, the pulmonary embolisms caused by the deep venous thrombosis are reduced, thus saving patients' lives

Reference signs in the drawings: 4: hydrogel; 11: first medicated thread; 12: first non-woven fabric; 13: first water absorption pad; 14: first suction pipe disk; 15: first negative pressure pipe; 16: first pressure reducing pipe; 17: first metal wire socket;

21: second medicated thread; 22: second non-woven fabric; 23: second water absorption pad; 24: second suction pipe disk; 25: second negative pressure pipe; 26: oxygen supply pipe; 27: rinser; 28: second metal wire socket;

311: third medicated thread; 312: third non-woven fabric; 313: third water absorption pad; 314: third suction pipe disk; 315: third negative pressure pipe; 316: third metal wire socket;

321: fourth medicated thread; 322: fourth non-woven fabric; 323: fourth water absorption pad; 324: air bag; 325: fourth metal wire socket.

DETAILED DESCRIPTION OF THE EMBODIMENTS

In order to make the objectives, technical solutions, and advantages of the present disclosure clearer, the present disclosure is further described below in detail in combination with the embodiments and the accompanying drawings of the specification. It should be understood that the specific embodiments described here are merely to explain the present disclosure, and not intended to limit the present disclosure.

On the contrary, the present disclosure covers any substitutions, modifications, equivalent teaching methods, and solutions defined by the claims within the spirit and scope of the present disclosure. Further, in order to enable the public to have a better understanding of the present disclosure, in the following detailed description of the present disclosure, some specific details are described in detail. Those skilled in the art can also fully understand the present disclosure without the description of these details.

It should be clear that the described embodiments are only a part of the embodiments of the present disclosure, rather than all of the embodiments. Based on embodiments of the present disclosure, all other embodiments obtained by those of ordinary skill in the art without creative work shall fall within the scope of protection of the present disclosure.

The terms used in the embodiments of the present disclosure are only for the purpose of describing the specific embodiments, and are not intended to limit the present disclosure. The singular forms of "a", "said", and "the" used in the embodiments of the present disclosure and the claims are also intended to include plural forms, unless the context clearly indicates other meanings.

Referring to FIG. 1 to FIG. 4, the present embodiment provides a medicated thread drainage treatment device. The treatment device includes:
- a first treatment unit used for postoperative pain relief, preferably multi-mode pain relief, wherein the multi-mode pain relief of the first treatment unit refers to clinically selecting a suitable pain relief mode from various pain relief modes, and the multi-mode pain relief includes two or more of electronarcosis for pain relief, infiltration anaesthesia, medicated thread drainage for pain relief, and paste penetration for pain relief;
- a second treatment unit used for promoting a wound to be quickly healed, wherein multiple therapies are preferably used to promote the wound to be quickly healed; promotion of quick healing of the wound by multiple therapies refers to clinically selecting suitable therapies from various methods that promote the wound to be quickly healed; the multiple therapies include promoting the blood circulation, electrical stimulation, oxygen supply, coverage with positive charges, and negative pressure extraction of hydrops in an operative area of the wound by means of a medicated thread;
- a third treatment unit used for preventing deep venous thrombosis, wherein multiple methods are preferably used to prevent the deep venous thrombosis, and include two or more of the following methods: (1) the wound is comprehensively drained with electric energy, the medicated thread, and negative pressure so that hydrops such as damaged tissue factors and fat granules in an operative area are extracted; (2) blood coagulation factors are electrically interfered to be quickly decomposed; (3) crus muscles are electrically stimulated, thus promoting muscle shrinkage and accelerating venous blood flow; (4) the electric energy accelerates healing, so the number of blood coagulation factors is reduced; (5) by electroanalgesia, activities cannot be affected; and (6) the crus is electrically pressed so that the returned blood volume is increased;
- an electropneumatic, negative-pressure, electric stimulation multipurpose therapy apparatus connected with the first treatment unit, the second treatment unit, and the third treatment unit and providing electropneumatic pressure, negative pressure, and electric energy.

A clinician can select the corresponding treatment unit according to a clinical need. The drugs in the first medicated thread in the first treatment unit are mostly analgesia and local anesthesia type drug formulas and are used for infiltration pain relief; the drugs in the second medicated thread in the second treatment unit are mostly wound healing type formulas and used for quickly healing the wound; and the drugs in the third treatment unit are mostly drug formulas for activating blood to dissipate stasis, and the medicated thread is plugged into the wound for anticoagulant drainage. The medicated thread drainage treatment device is used for realizing quick multi-mode pain relief of chronic complex wounds and postoperative wounds and realizing multi-therapy-based quick recovery and healing of the wounds. Multiple methods prevent the postoperative deep vein thrombi and the fat embolism, and the postoperative complications are greatly reduced; and particularly, the pulmonary embolisms caused by the deep venous thrombosis and the fat embolism are reduced, thus saving patients' lives.

Figure 1:
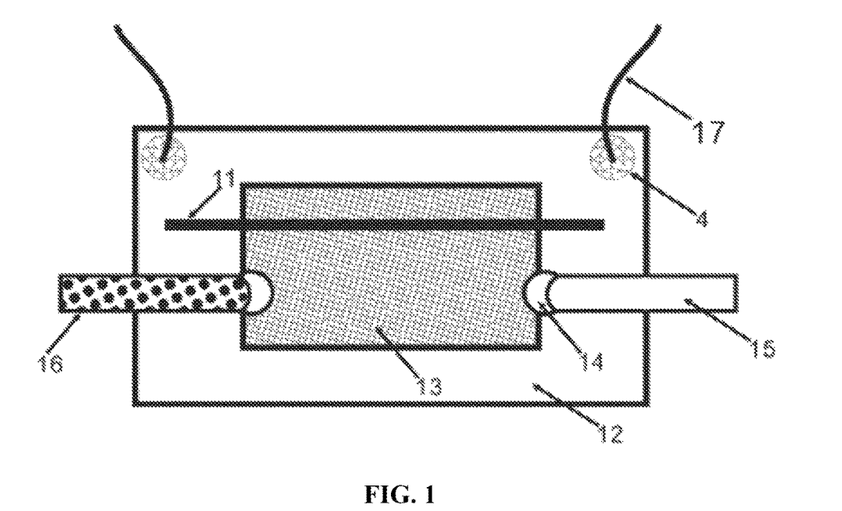
FIG. 1 is a schematic structural diagram of a first treatment unit in the embodiments of the present disclosure.

Referring to FIG. 1, in the present embodiment, the first treatment unit includes a first medicated thread, a first non-woven fabric, a first water absorption pad, two first suction pipe disks, a first negative pressure pipe used to be connected with a negative pressure suction device to suck liquid on the wound, a first pressure reducing pipe, and two first metal wire sockets;

the first water absorption pad is arranged at the middle position on the first non-woven fabric; the first medicated thread is arranged on the first water absorption pad; disk parts of the two first suction pipe disks are respectively arranged at two ends of the first water absorption pad; a pipe part of one first suction pipe disk is connected with the first negative pressure pipe, and a pipe part of the other first suction pipe disk is connected with the first pressure reducing pipe or a rinser; and the two first metal wire sockets (by means of hydrogel) are respectively arranged at two corners of the first non-woven fabric and are respectively connected with the electropneumatic, negative-pressure, electric stimulation multipurpose therapy apparatus.

In the present embodiment, first glue is uniformly coated on the first non-woven fabric on the surface with the first water absorption pad to fix the first medicated thread and the first water absorption pad which cover the wound.

In the present embodiment, the first water absorption pad is fixed on the first non-woven fabric through the first glue, and the first medicated thread is fixed on the first water absorption pad through the first glue.

In the present embodiment, the first medicated thread is not infiltrated with drugs when used in nonoperative wound, is infiltrated with lidocaine cream when used in wound infiltration anesthesia, and is infiltrated with a first blend when used in wound pain relief.

In the present embodiment, the first blend includes *rhizoma corydalis*, eggplants, *fructus meliae toosendan*, *rhizoma kaempferiae*, *rhizoma chuanxiong*, *Angelica sinensis*, *Rheum officinale*, *asarum*, *Ferula asafoetida*, olibanum, *Radix curcuma*, diclofenac sodium, semen strychni, borneol, cape jasmine, *Radix angelicae* dahuricae, and *Radix scutellariae*, each of which is 10 grams, fennel, myrrh, *Flos caryophylli*, red peony roots, *Radix aucklandiae*, cortex *phellodendri*, peppermint oil, and wintergreen oil, each of which is 5 grams, musk and capsicol, each of which is 3 grams, and 1 gram of diphenhydramine.

In the present embodiment, the first blend is mixed in the first glue.

Figure 2:
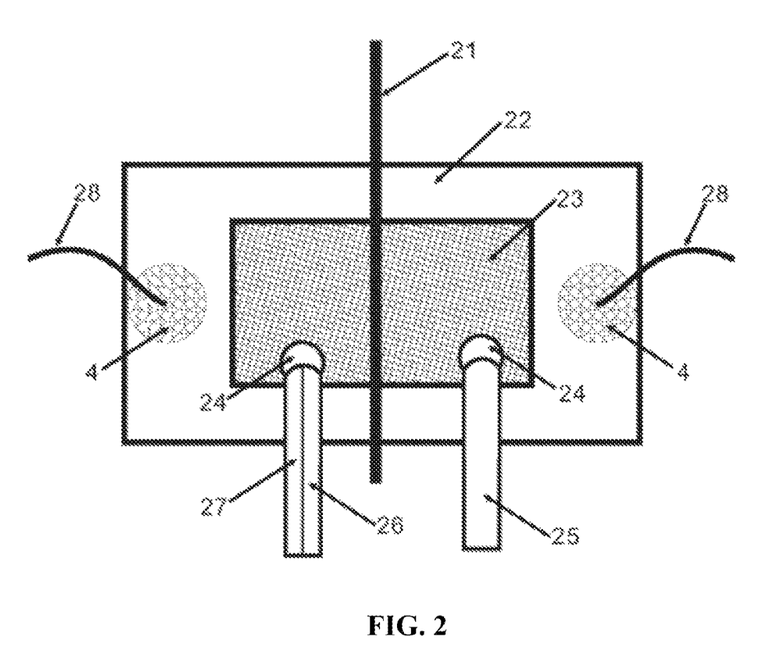
FIG. 2 is a schematic structural diagram of a second treatment unit in the embodiments of the present disclosure.

Referring to FIG. 2, in the present embodiment, the second treatment unit includes a second medicated thread, a second non-woven fabric, a second water absorption pad, two second suction pipe disks, a second negative pressure pipe used to be connected with a negative pressure suction device to suck liquid on the wound, an oxygen supply pipe used for supplying oxygen to the wound, a riser used for rinsing the wound, and two second metal wire sockets;

the second water absorption pad is arranged at the middle position on the second non-woven fabric; the second medicated thread is arranged on the second water absorption pad; disk parts of the two second suction pipe disks are respectively arranged at two ends of an edge of the same side of the second water absorption pad; a pipe part of one second suction pipe disk is connected with the second negative pressure pipe, and a pipe part of the other second suction pipe disk is connected with the oxygen supply pipe and the rinser, respectively; and the two second metal wire sockets (by means of hydrogel) are respectively disposed on the second non-woven fabric and arranged on two sides of the second water absorption pad and are respectively connected with the electropneumatic, negative-pressure, electric stimulation multipurpose therapy apparatus.

In the present embodiment, a second blend or metal ions is or are adhered on the second medicated thread.

In the present embodiment, the second water absorption pad is fixed on the second non-woven fabric through the second glue, and the second medicated thread is fixed on the second water absorption pad through the second glue.

In the present embodiment, the second glue is uniformly coated on the second non-woven fabric on the surface with the second water absorption pad to fix the second medicated thread and the second water absorption pad which cover the wound.

In the present embodiment, a second blend or metal ions is or are mixed in the second glue.

In the present embodiment, the second blend includes natural calculus bovis, camphor, pearls, red halloysite, amber, lead monoxide, olibanum, and myrrh, each of which is 8 grams, calcined calamine, calcined plaster, keels, and calomel, each of which is 15 grams, and 15 grams of borneol.

Figure 3:
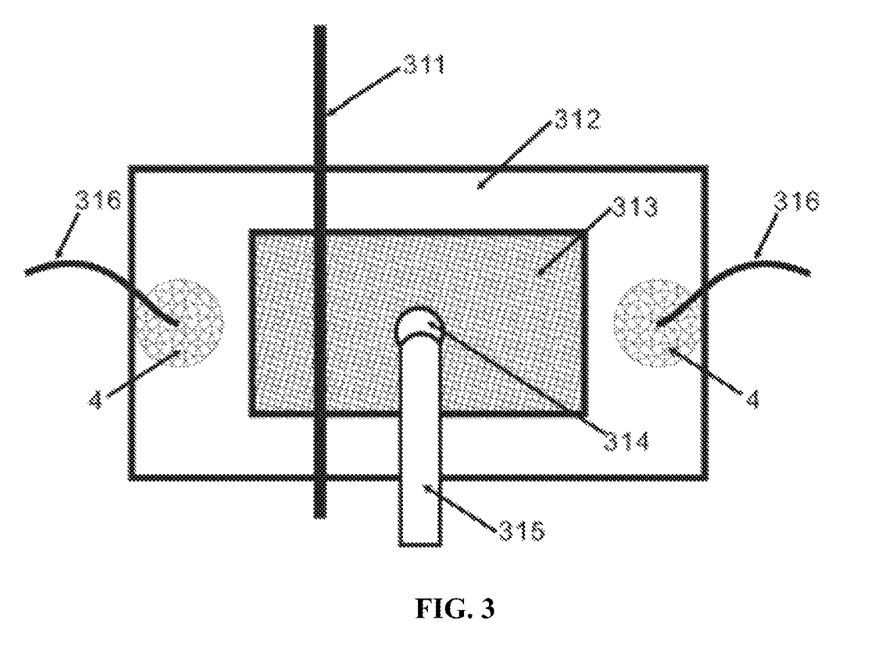
FIG. 3 is a schematic structural diagram of a third treatment unit in the embodiments of the present disclosure.
Figure 4:
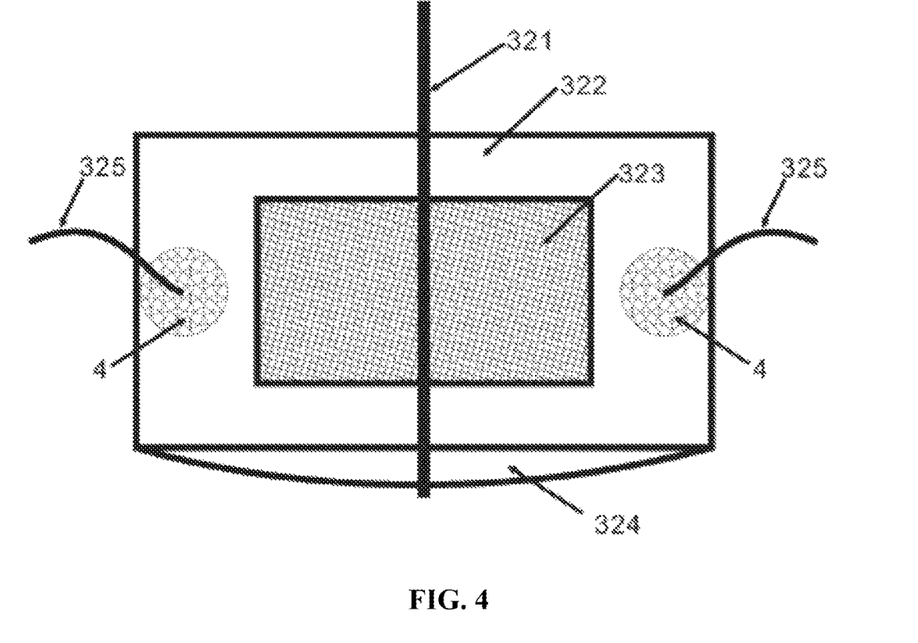
FIG. 4 is a schematic structural diagram of an auxiliary treatment module of a third treatment unit in the embodiments of the present disclosure.

In the present embodiment, the third treatment unit includes a wound treatment module used on the wound and two auxiliary treatment modules pasted on the crus muscles of the lower extremities;
the wound treatment module and the auxiliary treatment modules are respectively connected with the electropneumatic, negative-pressure, electric stimulation multipurpose therapy apparatus.

In the present embodiment, the wound treatment module and the auxiliary treatment modules are respectively connected with the electropneumatic, negative-pressure, electric stimulation multipurpose therapy apparatus, so that wound seepage will not be coagulated by means of electrostimulation and the medicated thread and drained smoothly; the redundant blood coagulation factors and the hydrops in the operative area are extracted from the wound and prevented from entering the blood to cause the deep venous thrombosis.

In the present embodiment, a method for preventing the deep venous thrombosis by the third treatment unit includes the following steps: (1) the wound is comprehensively drained with the electric energy, the medicated thread, and the negative pressure so that the hydrops and damaged tissues in the operative area seep; (2) blood coagulation factors are electrically interfered to be quickly decomposed; (3) the crus muscles are electrically stimulated, thus promoting muscle shrinkage and accelerating venous blood flow; (4) the electric energy accelerates healing, so the number of blood coagulation factors is reduced; (5) by electroanalgesia, activities cannot be affected; and (6) the crus is electrically pressed so that the returned blood volume is increased.

Referring to FIG. 3, in the present embodiment, the wound treatment module includes a third medicated thread, a third non-woven fabric, a third water absorption pad, a third suction pipe disk, a third negative pressure pipe used to be connected with a negative pressure suction device to suck liquid on the wound, and two third metal wire sockets;
the third water absorption pad is arranged at the middle position on the third non-woven fabric; the third medicated thread is arranged on the third water absorption pad; the third suction pipe disk is arranged at the middle part on the third water absorption pad and is connected with the third negative pressure pipe; and the two third metal wire sockets (by means of hydrogel) are respectively disposed on the third non-woven fabric and arranged on two sides of the third water absorption pad and are respectively connected with the electropneumatic, negative-pressure, electric stimulation multipurpose therapy apparatus.

Referring to FIG. 4, in the present embodiment, each auxiliary treatment module includes a fourth medicated thread, a fourth non-woven fabric, a fourth water absorption pad, an air bag, and two fourth metal wire sockets;
the fourth water absorption pad is arranged at the middle position on the fourth non-woven fabric; the fourth medicated thread is arranged on the fourth water absorption pad; the two fourth metal wire sockets (by means of hydrogel) are respectively disposed on the fourth non-woven fabric and arranged on two sides of the fourth water absorption pad and are respectively connected with the electropneumatic, negative-pressure, electric stimulation multipurpose therapy apparatus; and the air bag is arranged on the other surface of the fourth non-woven cloth that is opposite to the fourth water absorption pad.

In the present embodiment, the third medicated thread is blended with a third blend used for treating hypercoagulable high-risk patients and having an effect of activating blood circulation to dissipate stasis;
the third blend includes pseudo-ginseng, *Flos carthami, fructus citri, Radix astragali, Radix codonopsis, rhizoma chuanxiong, pericarpium citri reticulatae viride,* semen *pruni persicae, Radix paeoniae rubra, fructus aurantii,* and *rhizoma cyperi,* each of which is 10 grams, *salvia miltiorrhiza,* pollen typhae, white atractylodes rhizome, yam, olibanum, *Radix bupleuri,* toosendan fruit, *Radix pseudostellariae,* and prepared *Radix* licorice, each of which is 8 grams, and 1 gram of acetylsalicylic acid.

In the present embodiment, the third medicated thread is used for treating non-hypercoagulable low-risk patients when it is not blended with the third blend.

In the present embodiment, the hydrogel is blended with the metal ions. When covering the wound, the hydrogel blended with the metal ions adsorbs and activates negatively charged growth factors and protease to be accumulated towards the wound to accelerate healing of the wound.

In the present embodiment, the metal ions are the potassium ions or mixed ions of the potassium ions, sodium ions, calcium ions, and magnesium ions.

In the present embodiment, a main physiological function of the potassium ions is to maintain the metabolism of cells and activate the activity of the protease;
the sodium ions contribute to the normal operation of nerves and muscles in the body;

the calcium ions are blood coagulation factors and activate the blood coagulation factors to participate in a coagulation process;

the magnesium ions are used for activating the activities of various human enzymes.

In the present embodiment, the fourth medicated thread is blended with the third blend or is not blended with any drug.

In the present embodiment, the first non-woven fabric, the second non-woven fabric, the third non-woven fabric, and the fourth non-woven fabric can all be replaced by PU films.

The medical thread drainage treatment device provided by the embodiments of the present disclosure has been described in detail above. The illustration of the above embodiments is only used to help understand the method of the present disclosure and the core idea of the method. Meanwhile, for those of ordinary skill in the art, according to the idea of the present disclosure, there will be changes in the specific implementation modes and the scope of application. Therefore, the content of this specification should not be construed as a limitation to the present disclosure.

For example, certain words are used in the specification and claims to refer to specific assemblies. Those skilled in the art should understand that hardware manufacturers may use different names to refer to the same assembly. This specification and claims do not use differences in names as a way to distinguish assemblies, but use differences in functions of assemblies as a criterion for distinguishing. If "including" or "comprising" mentioned in the entire specification and claims is an open term, it should be interpreted as "including/comprising but not limited to". "Approximately" means that within an acceptable error range, those skilled in the art can solve the technical problem within a certain error range and basically achieve the technical effect. The following description of the specification is a preferred implementation mode for implementing the present disclosure. The description is based on the general principle for illustrating the present disclosure and is not intended to limit the scope of the present disclosure. The protection scope of the present disclosure shall be subject to those defined by the appended claims.

It should be further noted that the terms "comprise", "include", or any other variation thereof are intended to cover a non-exclusive inclusion, so that an article or system that includes a list of elements includes those elements and further includes other elements not expressly listed or further includes elements inherent to such an article or system. Without more constraints, an element preceded by "includes a . . . " does not preclude the existence of additional identical elements in the article or system that includes the element.

It should be understood that the term "and/or" herein is only an association relationship that describes associated objects, and represents that there can be three relationships. For example, A and/or B can represent that: A exists alone, A and B exist simultaneously, and B exists alone. In addition, the character "/" herein generally indicates that the front and back associated objects are in an "or" relationship.

The above description shows and describes several preferred embodiments of the present disclosure. However, as mentioned above, it should be understood that the present disclosure is not limited to the form disclosed herein and should not be regarded as the exclusion of other embodiments, but can be used for various other combinations, modifications, and environments. The present disclosure can be changed within the conceived scope of this application by means of the above teachings or technologies or knowledge in the related art. The modifications and changes made by those skilled in the art do not depart from the spirit and scope of the present disclosure, and shall all fall within the protection scope of the appended claims of the present disclosure.

What is claimed is:

1. A medicated thread drainage treatment device, wherein the treatment device comprises a first treatment unit used for postoperative pain relief, electric energy transmission, and retrograde drainage; a second treatment unit used for promoting quick healing of the wound; a third treatment unit used for preventing deep venous thrombosis; and an electropneumatic negative pressure electric energy stimulation multipurpose therapy apparatus respectively connected with the first treatment unit, the second treatment unit, and the third treatment unit and providing electropneumatic pressure, negative pressure, and electric energy; the first treatment unit comprises a first medicated thread, a first non-woven fabric, a first water absorption pad, two first suction pipe disks, a first negative pressure pipe used to be connected with a negative pressure suction device and sucks liquid on a wound, a first pressure reducing pipe or a rinser; two first metal wire sockets, wherein the first water absorption pad is arranged at the middle position on the first non-woven fabric; the first medicated thread is arranged on the first water absorption pad or in a negative pressure drainage pipe; disk parts of the two first suction pipe disks are respectively arranged at two ends of the first water absorption pad; a pipe part of one first suction pipe disk is connected with the first negative pressure pipe, and a pipe part of the other first suction pipe disk is connected with the first pressure reducing pipe or a rinser; and the two first metal wire sockets are respectively arranged at two corners of the first non-woven fabric by means of hydrogel and are respectively connected with the electropneumatic, negative-pressure, electric stimulation multipurpose therapy apparatus.

2. The medicated thread drainage treatment device according to claim 1, wherein first glue is uniformly coated on the first non-woven fabric on the surface with the first water absorption pad to fix the first medicated thread and the first water absorption pad which cover the wound.

3. The medicated thread drainage treatment device according to claim 1, wherein the first medicated thread is not infiltrated with drugs when used in a nonoperative wound, is infiltrated with lidocaine cream when used in wound infiltration anesthesia, and is infiltrated with a first blend when used in wound pain relief.

4. The medicated thread drainage treatment device according to claim 1, wherein the second treatment unit comprises a second medicated thread, a second non-woven fabric, a second water absorption pad, two second suction pipe disks, a second negative pressure pipe used to be connected with a negative pressure suction device to suck liquid on the wound, an oxygen supply pipe used for supplying oxygen to the wound, a riser used for rinsing the wound, and two second metal wire sockets; the second medicated thread may also be arranged in a second negative pressure pipe and soaked in anticoagulant medicinal liquor; the second water absorption pad is arranged at the middle position on the second non-woven fabric; the second medicated thread is arranged on the second water absorption pad; disk parts of the two second suction pipe disks are respectively arranged at two ends of an edge of the same side of the second water absorption pad; a pipe part of one second suction pipe disk is connected with the second negative pressure pipe, and a pipe part of the other second suction pipe disk is connected with the oxygen supply pipe and the rinser, respectively; the suction pipe disks may also be replaced by drainage pipes; the two second metal wire sockets are respectively disposed on the second non-woven fabric by means of hydrogel and arranged on two sides of the second water absorption pad and are respectively connected with the electropneumatic, negative-pressure, electric stimulation multipurpose therapy apparatus.

5. The medicated thread drainage treatment device according to claim 4, wherein the second medicated thread is adhered with a second blend or metal ions and is plugged into the operative area; and effusions in the operative area are drained in a retrograde manner by means of energy conduction resonance of the medicated thread and the potassium ions of the hydrogel.

6. The medicated thread drainage treatment device according to claim 1, wherein the third treatment unit comprises a wound treatment module used on the wound and two auxiliary treatment modules pasted on the crus muscles of both lower extremities; the wound treatment module and the auxiliary treatment modules are respectively connected with the electropneumatic, negative-pressure, electric stimulation multipurpose therapy apparatus.

7. The medicated thread drainage treatment device according to claim 6, wherein the wound treatment module comprises a third medicated thread, a third non-woven fabric, a third water absorption pad, a third suction pipe disk, a third negative pressure pipe used to be connected with a negative pressure suction device to suck liquid on the wound, and two third metal wire sockets; the third water absorption pad is arranged at the middle position on the third non-woven fabric; the third medicated thread is arranged on the third water absorption pad; the third suction pipe disk is arranged at the middle part on the third water absorption pad and is connected with the third negative pressure pipe; and the two third metal wire sockets are respectively disposed on the third non-woven fabric by means of the hydrogel and arranged on two sides of the third water absorption pad and are respectively connected with the electropneumatic, negative-pressure, electric stimulation multipurpose therapy apparatus.

8. The medicated thread drainage treatment device according to claim 6, wherein each auxiliary treatment module comprises a fourth medicated thread, a fourth non-woven fabric, a fourth water absorption pad, an air bag, and two fourth metal wire sockets; the fourth water absorption pad is arranged at the middle position on the fourth non-woven fabric; the fourth medicated thread is arranged on the fourth water absorption pad; the two fourth metal wire sockets are respectively disposed on the fourth non-woven fabric by means of the hydrogel and arranged on two sides of the fourth water absorption pad and are respectively connected with the electropneumatic, negative-pressure, electric stimulation multipurpose therapy apparatus; and the air bag is arranged on the other surface of the fourth non-woven cloth that is opposite to the fourth water absorption pad.

9. The medicated thread drainage treatment device according to claim 7, wherein the third medicated thread is blended with a third blend used for treating hypercoagulable high-risk patients and having an effect of activating blood circulation to dissipate stasis.

\* \* \* \* \*